(12) United States Patent
Wong et al.

(10) Patent No.: US 10,222,307 B2
(45) Date of Patent: Mar. 5, 2019

(54) MIXING AND TRANSFER DEVICE FOR MATERIALS USED IN BIOLOGICAL AND BIOCHEMICAL ASSAYS

(71) Applicant: Credo Biomedical Pte Ltd., Singapore (SG)

(72) Inventors: Jr Winston Wong, New Taipei (TW); Stephen Chang-Chi Kao, New Taipei (TW); Ying-Ta Lai, New Taipei (TW); Ming-Fa Chen, New Taipei (TW); Sheng-Pin Hsiao, New Taipei (TW)

(73) Assignee: Credo Biomedical Pte Ltd., Singapore (SG)

( * ) Notice: Subject to any disclaimer, the term of this patent is extended or adjusted under 35 U.S.C. 154(b) by 195 days.

(21) Appl. No.: 15/586,302

(22) Filed: May 4, 2017

(65) Prior Publication Data

US 2017/0336304 A1 Nov. 23, 2017

Related U.S. Application Data

(60) Provisional application No. 62/337,886, filed on May 18, 2016.

(51) Int. Cl.
*B01D 63/16* (2006.01)
*B01F 9/00* (2006.01)
(Continued)

(52) U.S. Cl.
CPC ............. *G01N 1/38* (2013.01); *B01D 63/16* (2013.01); *B01F 9/0003* (2013.01); *B01F 15/06* (2013.01);
(Continued)

(58) Field of Classification Search
CPC .... B01D 63/16; B01F 15/06; B01F 2015/061; B01F 2215/0037; B01F 9/0003;
(Continued)

(56) References Cited

U.S. PATENT DOCUMENTS

| 9,586,206 B2 | 3/2017 | Croisard | |
| 2005/0083781 A1* | 4/2005 | Caren | B01F 5/061 366/220 |

(Continued)

FOREIGN PATENT DOCUMENTS

| JP | S55-155234 A | 12/1980 |
| JP | H4-47268 A | 2/1992 |

(Continued)

*Primary Examiner* — Jennifer Wecker
(74) *Attorney, Agent, or Firm* — Winston Hsu

(57) ABSTRACT

A mixing device for operating biological, chemical or biochemical materials used in an assay includes a mixing member formed with a plurality of chambers, each having a sealable port provided along an edge of the mixing member. The mixing device also includes one or more compartments that are movable along the edge of the mixing member between selected ones of the sealed chambers. This compartment is operable to receive materials from and transfer materials between the chambers. Selected ones of the chambers include associated processing elements, for example, including heating and cooling elements, magnetic elements, membranes and lateral flow devices. The mixing device is also pivotable, for example, to facilitate the application of gravity force in the transfer of materials between the chambers and one or more compartments. The mixing device may operate manually by hand-held unit. Also, this mixing device may operate automatically with at least one driving unit.

78 Claims, 15 Drawing Sheets

(51) Int. Cl.
  G01N 1/00 (2006.01)
  G01N 1/44 (2006.01)
  G01N 1/02 (2006.01)
  G01N 1/38 (2006.01)
  B01F 15/06 (2006.01)
  G01N 1/40 (2006.01)
  G01N 33/558 (2006.01)
  B01F 7/00 (2006.01)
  G01N 21/75 (2006.01)
  G01N 35/00 (2006.01)

(52) U.S. Cl.
  CPC ............... G01N 1/02 (2013.01); G01N 1/405 (2013.01); G01N 1/44 (2013.01); G01N 33/558 (2013.01); *B01F 7/008* (2013.01); *B01F 2015/061* (2013.01); *B01F 2215/0037* (2013.01); *G01N 2001/002* (2013.01); *G01N 2001/386* (2013.01); *G01N 2021/752* (2013.01); *G01N 2035/00564* (2013.01)

(58) Field of Classification Search
  CPC . B01F 7/008; G01N 1/02; G01N 1/38; G01N 1/405; G01N 1/44; G01N 2001/002; G01N 2001/386; G01N 2035/00564; G01N 33/558; G01N 2021/752
  See application file for complete search history.

(56) References Cited

U.S. PATENT DOCUMENTS

2011/0117665 A1* 5/2011 Saiki ................. B01L 3/502715
                                                                436/164
2013/0089858 A1   4/2013 Wong, Jr.

FOREIGN PATENT DOCUMENTS

| JP | H11-226304 A | 8/1999 |
| JP | 2013-510294 A | 3/2013 |
| JP | 2013-542426 A | 11/2013 |
| JP | 2014-527183 A | 10/2014 |
| WO | 2011056165 A1 | 5/2011 |

* cited by examiner

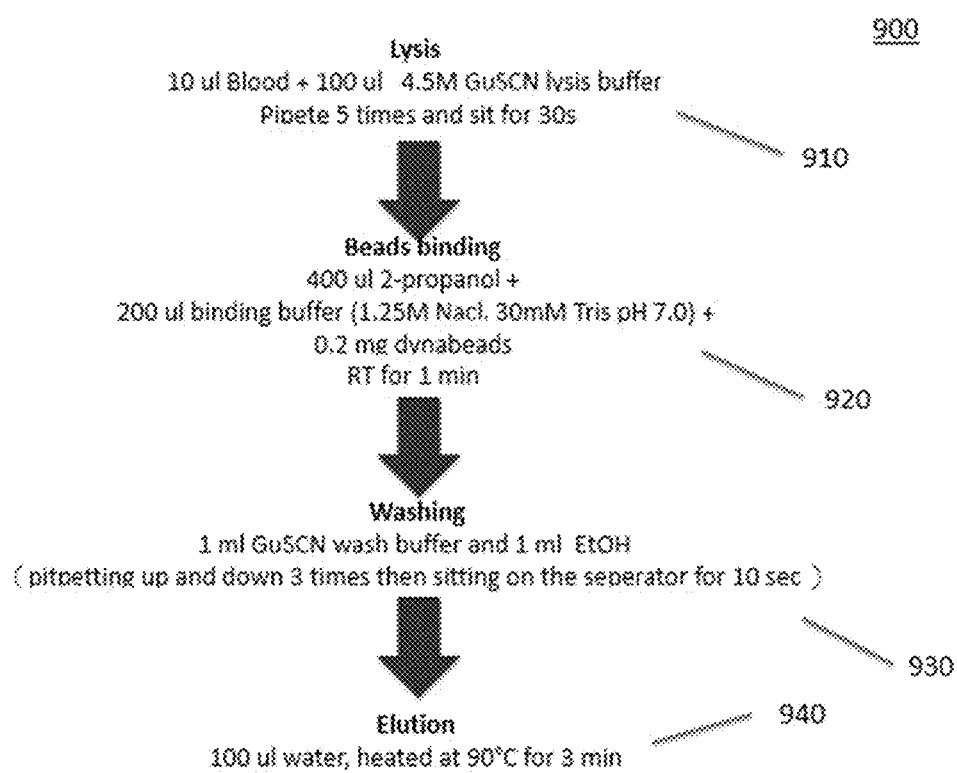

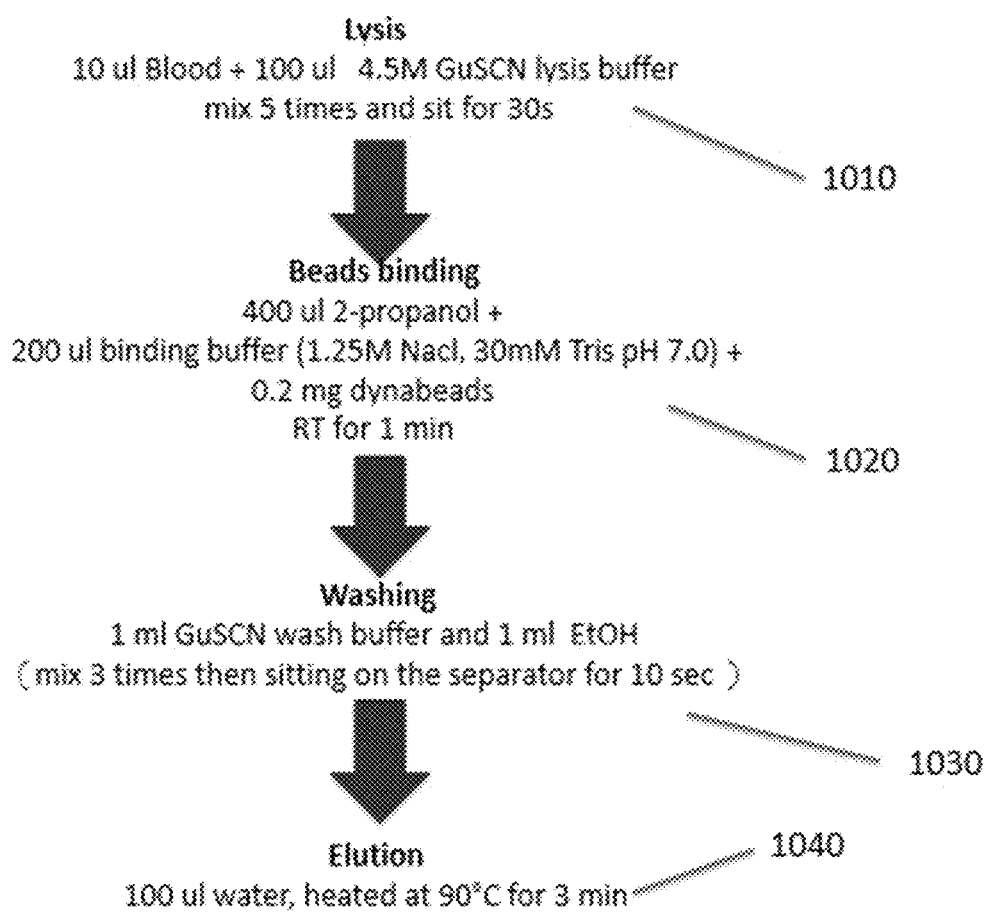

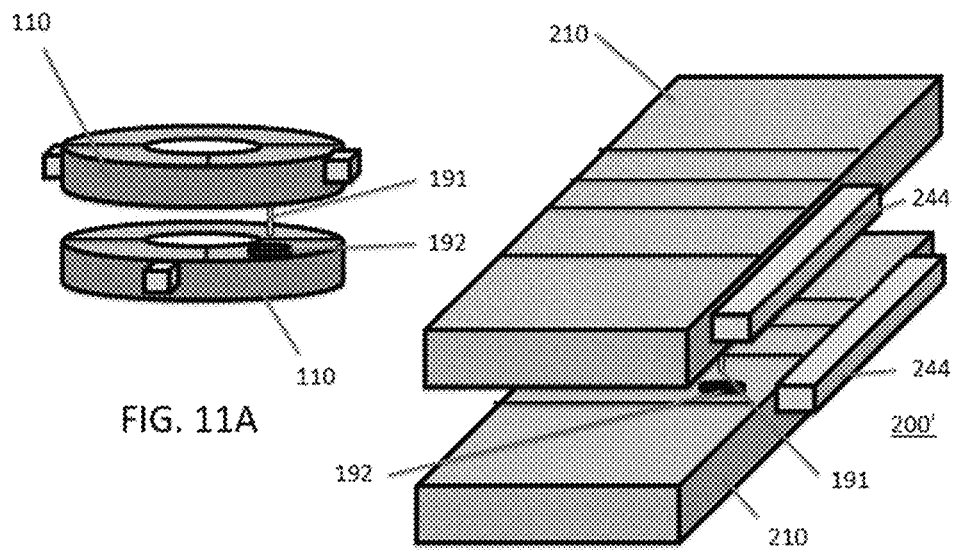

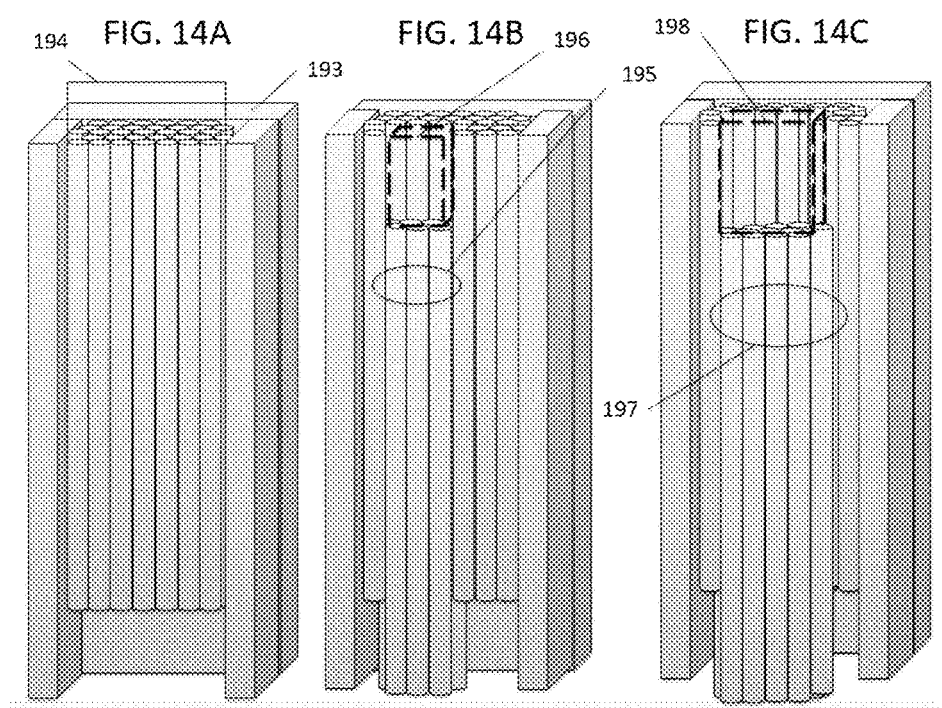

MIXING AND TRANSFER DEVICE FOR MATERIALS USED IN BIOLOGICAL AND BIOCHEMICAL ASSAYS

CROSS REFERENCE TO RELATED APPLICATIONS

This application claims the benefit of priority of U.S. Provisional Application No. 62/337,886 filed on May 18, 2016, and included herein by reference.

BACKGROUND OF THE INVENTION

1. Field of the Invention

This disclosure pertains to a device for carrying out biological, chemical or biochemical reactions requiring mixing, heating and cooling steps, and more particularly, to a mixing and transfer device for automating biological and biochemical assays, including preparation of materials used to perform such assays. This device may operate manually or automatically.

2. Description of the Prior Art

Many biological or biochemical assays require that certain preparatory steps be carried out on the materials that are subject to assay. These preparatory steps may include, for example, adding certain additional materials, and undertaking certain purification steps and washing steps. To date, these preparatory steps and steps in performing the assays themselves have been carried out manually, and as such have been both time consuming and error prone.

SUMMARY OF THE INVENTION

Briefly, aspects of the present disclosure are directed to a mixing device for manipulating biological, chemical and biochemical materials, for example as may be used in a biological or biochemical assay. The mixing device includes a mixing member with a plurality of chambers, each having at least one chamber port provided along a side edge of the mixing member. The chamber ports may be selectively configured in either an open state or a closed state.

The mixing device may operate manually by hand-held unit. Also, this mixing device may operate automatically with at least one driving unit.

The mixing device further includes at least one compartment which is movable along the side edge for selective positioning in proximity to the chamber ports. The compartment includes a compartment port along a side of the compartment facing the side edge of the mixing member. When the compartment port is positioned in overlapping proximity to the chamber port of a selected one of the chambers, the state of the chamber port of the selected chamber is changed from a closed state to an open state and the state of at least one of the chamber ports for another one of the plurality of chambers remains unchanged. In this state, an interior volume of the at least one compartment is placed in fluid communication with an interior volume of the selected chamber, enabling material to be transferred from the selected chamber to the one compartment.

The compartment can then be moved in overlapping proximity to another one of the chambers, such that the interior volume of the one compartment is placed in fluid communication with an interior volume of the other chamber, enabling material to be transferred from the one compartment to the other chamber. In this manner, materials can be transferred among the chambers in the mixing member.

According to one aspect of the present disclosure, one or more of the plurality of chambers may include an electromagnetic element.

According to another aspect of the present disclosure, one or more of the plurality of chambers may include a heating or cooling element.

According to another aspect of the present disclosure, the mixing member may be formed as a toroidal ring of radially-arrayed chambers, and the mixing device may include at least one rotational driving unit for spinning one or more of the ring and the at least one compartment, and/or for selectively positioning the compartment in proximity to one or more of the chamber ports.

According to another aspect of the present disclosure, the mixing device may further include an inner chamber abutting an interior edge of the mixing member formed as a toroidal ring.

According to yet another aspect of the present disclosure, the mixing member may include two opposing, linearly-extending planar side edges along which chamber ports of the chambers are positioned, and two compartments respectively in proximity to the two opposing, linearly-extending planar side edges.

According to another aspect of the present disclosure, the mixing member including the two opposing, linearly-extending planar side edges may further include: a driving unit for translatable moving one or more of the mixing member or the carrier.

According to another aspect of the present disclosure, the mixing device may further include a plurality of mixing members vertically positioned relative to one another.

According to yet another aspect of the present disclosure, the mixing device may include a fixture for operably positioning the mixing member, a driving unit and one or more compartments relative to one another; and a pivoting member coupled to the fixture for selectively positioning the mixing device in at least in vertical and horizontal positions.

According to another aspect of the present disclosure, a method for operating a biological, chemical and biochemical materials includes: i) placing a material in an interior volume of one of a plurality of sealed chambers provided in a mixing member, each chamber having a sealable port along at least one side edge of a respective mixing member, ii) transferring the material in the interior volume of the one chamber to an interior volume of an outer compartment positioned in proximity to the one chamber port, iii) moving the outer compartment in proximity to a second chamber port, and iv) transferring the material in the interior volume of the outer compartment to an interior volume of the second chamber.

This SUMMARY is provided to briefly identify some aspects of the present disclosure that are further described below in the DESCRIPTION. This SUMMARY is not intended to identify key or essential features of the present disclosure nor is it intended to limit the scope of any claims.

The term "aspects" is to be read as "at least one aspect." The aspects described above and other aspects of the present disclosure described herein are illustrated by way of example(s) and not limited in the accompanying drawing.

These and other objectives of the present invention will no doubt become obvious to those of ordinary skill in the art after reading the following detailed description of the preferred embodiment that is illustrated in the various figures and drawings.

BRIEF DESCRIPTION OF THE DRAWINGS

A more complete understanding of the present disclosure may be realized by reference to the accompanying drawing in which:

FIG. 9 is a flow diagram illustrating a conventional manual process for preparing a blood product for assay;

FIG. 10B is a flow diagram illustrating the automated process employed by the mixing device of FIG. 10A;

FIGS. 11A and 11B are schematic diagrams respectively illustrating stacked arrangements of the mixing devices depicted in FIGS. 1 and 7, in accordance with aspects of the present disclosure;

FIGS. 14A-14C are schematic diagrams illustrating additional aspects relating to the positioning of an outer compartment of mixing device illustrated by FIGS. 12A and 12B.

DETAILED DESCRIPTION

The following merely illustrates the principles of the disclosure. It will thus be appreciated that those skilled in the art will be able to devise various arrangements which, although not explicitly described or shown herein, embody the principles of the disclosure and are included within its spirit and scope.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements later developed that perform the same function, regardless of structure.

Unless otherwise explicitly specified herein, the drawings are not drawn to scale.

We now provide some non-limiting, illustrative examples that illustrate operational aspects of a mixing device and associated method preparing materials used in biological or biochemical assays.

As used herein, directional terms as may be used such as "horizontal," "vertical," "proximal," "distal," "front", "rear", "left," "right," "inner," "outer," "interior" and "exterior" relate to an orientation of the disclosed mixing device from the perspective of a typical user, and do not specify permanent, intrinsic features or characteristics of the device.

Aspects of the present disclosure describe a mixing device for carrying out biological, chemical and biochemical reactions, including applications directed to preparing materials used in biological or biochemical assays. While described in this context, it is contemplated that aspects of the disclosed mixing device may be easily applied to preparing other types of materials and/or to carry out other types of reactions, for example including DNA extraction reactions involving polymerase chain reactions (PCRs) and chemical reactions associated with testing water chemistry and biologics.

Also, aspects of the present disclosure describe a mixing device operated automatically with at least one driving unit. However, one of the skill in the art will readily understand that the present invention may operate manually by using a hand-held unit, for example a handle, a knob, a lever, or a rotation handles.

Figure 1:
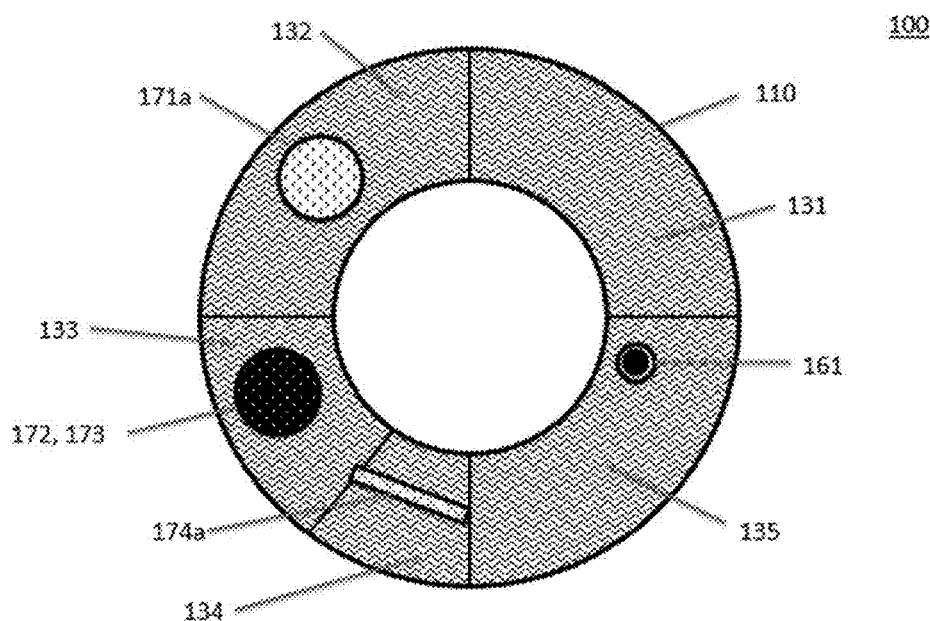
FIG. 1 is a schematic diagram illustrating a first configuration of a mixing device according to aspects of the present disclosure.

In accordance with aspects of the present disclosure, FIG. 1 illustrates a first exemplary mixing device 100. The mixing device 100 includes a series of sealed chambers 131-135 that are arrayed in a toroidal ring 110. As illustrated, several of the sealed chambers (chambers 131, 132 and 135) comprise uniform radial quarter-segments of the ring. Others of the sealed chambers (chambers 133, 134) together comprise non-uniform radial segments of the ring 110. One of skill in the art will readily understand that a variety of numbers and configurations of the sealed chambers 131-135 are contemplated by the present disclosure, and may be sized for example to store liquid or solid materials of a particular volume or mass. Optionally, the numbers and sizes of the sealed chambers 131-135 may be varied by employing adjustable inner walls that separate the chambers.

Access to the sealed chambers may be provided in a variety of ways, including for example by means of an interactive port 161 which as illustrated is provided in an upper surface of the sealed chamber 135. The interactive port 161 may for example provide access to an instrument such as a syringe or pipette for depositing or removing materials from the chamber, an is preferably self- sealing upon removal of the instrument from the chamber. Commercially-available seals which are suitable for use in such ports may include, for example, SLITSEAL self-closing seals from Eicom USA, San Diego, Calif., USA. Alternatively, a conventional valve element for bladders used in footballs, basketballs and other sporting goods may be used for this purpose.

In addition to providing access for depositing or removing materials, the interactive port 161 may provide access for the addition or removal of an associated gaseous material in order to increase or decrease a pressure in the sealed chamber 135. Pressure may be increased or decreased, for example, to promote a material flow into, out of or across the chamber 135.

A variety of components may be provided within the interior of the sealed chambers to assist with the material preparation. As illustrated with reference to the sealed chamber 134 of FIG. 1, a membrane 174*a* may provide filtration, separation and related functions. Typical biologic applications well suited to membranes include separating nucleic acid material from a biological material and separating plasma from whole blood. Suitable membrane materials for biologic applications are commercially available, for example, from Pall Corporation of Port Washington, N.Y.

As illustrated with reference to the sealed chamber 133 of FIG. 1, a heating element 172 or cooling element 173 may be provided to meet various thermal requirements. Suitable elements 172, 173 for this purpose may, for example, include Peltier heating and cooling components such as are commercially available from CUI Inc. of Tualatin, Oreg. Heating and cooling components may be advantageously used, for example, for thermal cycling in PCR reactions and other reactions requiring isothermal amplification.

As an alternative to elements 172, 173, heating or cooling of the chambers 131-135 may be achieved by forming the chambers from a thermally conductive material (for example, a thermally conductive polymer such as is available from Celanese Corporation of North Kingstown, R.I.) and providing external heating or cooling sources that can be applied to a selected one of the chambers 131-135. Suitable external heating or cooling sources are commercially available, for example, from Thermo Fisher Scientific Inc. of Waltham, Mass.

With reference to the sealed chamber 132 of FIG. 1, an electromagnetic element 171*a* may be provided for example to facilitate movement of magnetically-active materials into and/or out of the chamber. Suitable electromagnetic elements 171*a* are commercially available from APW Company of Rockaway, N.J. As an alternative, a paramagnetic material may be provided within the sealed chamber 132 for activation via an external electromagnetic source placed in proximity to the sealed chamber 132. Suitable paramagnetic materials may, for example, include aluminum or platinum. External electromagnetic sources are commercially available, for example, from AEC Magnetics of Cincinnati, Ohio.

Figure 2:
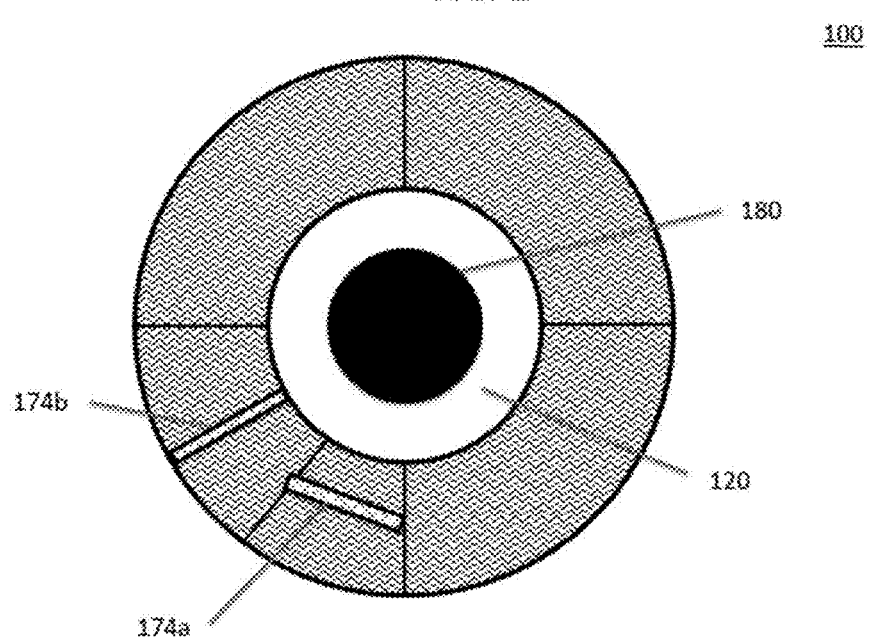
FIG. 2 is a schematic diagram illustrating additional aspects of the present disclosure.

FIG. 2 further illustrates features of the mixing device 100. In particular, FIG. 2 illustrates an additional membrane element 174*b* that is positioned radially relative to a longitudinal axis of the mixing device 100. In addition, FIG. 2 illustrate a rotational driving element 180 that may be used to rotate the ring 110, for example, about the longitudinal axis to move the material contents of one of more chambers outwardly in response to the application of centripetal force. The rotational driving element is surrounded by an inner chamber 120. The rotational driving element 180 may be preferably based on a conventional servo motor-based driving unit available, for example, from Baldor Electric Company, Fort Smith, Ark.

In accordance with aspects of the present disclosure, components of the driving element 180 may include one or more axles, drive wheels and/or gear sets for coupling the motor to one or more of the ring 110 or the inner chamber 120, and may be adapted as required for handling different configurations of the ring 110 and inner chamber 120. Additional driving components may be provided to pivot the longitudinal axis (for example, rotating this axis by 90 degrees to enable a gravity-induced transfer of materials between the inner chamber 120 and ring 110). Operation of the rotational driving element 180 is preferably managed by a programmable logic controller as may be available, for example, from Siemens AG, Munich, Germany.

Figure 3A:
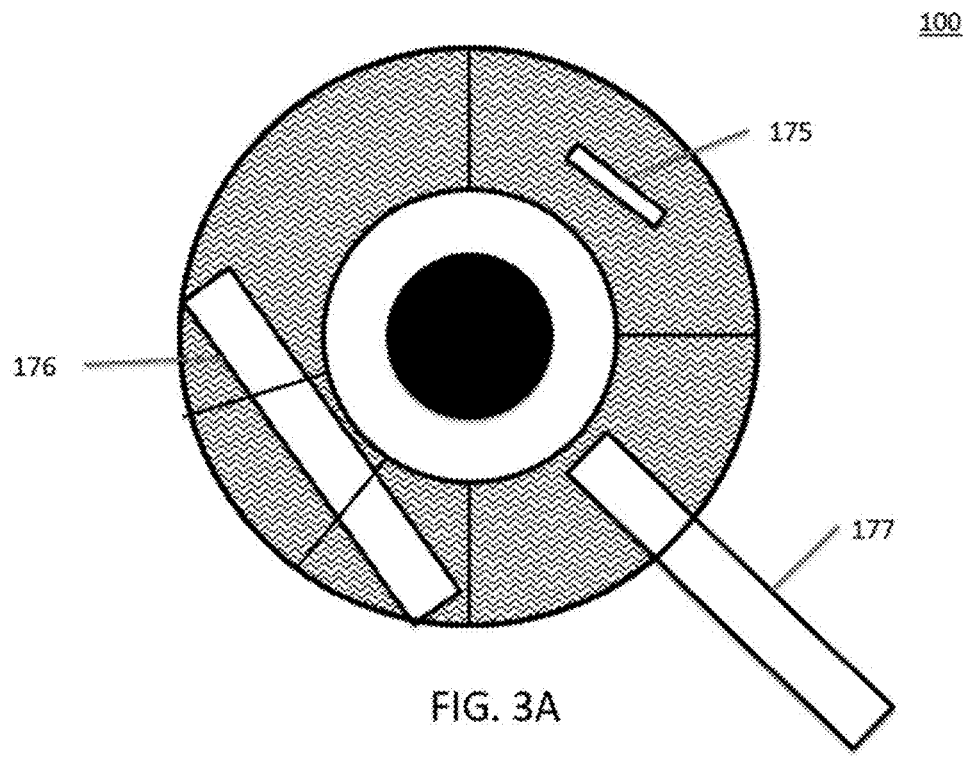
FIG. 3A is a schematic diagram illustrating further aspects of the present disclosure.

FIG. 3A illustrates lateral flow devices (LFDs) 175, 176 and 177, which may be included as additional elements of the mixing device 100 that provide for the detection and movement of certain components of the materials deposited in the sealed chambers. One type of LFD that may be preferably used with the mixing device 100 is more fully described in related International Patent Application Nos. PCT/IB2014/002637 ("Assay Test Device, Kit and Method of Using") filed Aug. 28, 2014 and PCT/US2012/055542 ("Molecular Diagnostic Assay Device and Method of Use") filed Sep. 14, 2012, each of which being hereby incorporated by reference in its entirety herein. This type of LFD is particularly well-suited for reactions requiring additional steps (for example, including enzyme-linked immunosorbent assay (ELISA) tests which add an enzyme substrate to the LFD after the fluid flows are complete in order for a change in color to be expressed by the substrate for identifying a target analyte).

Figure 3B:
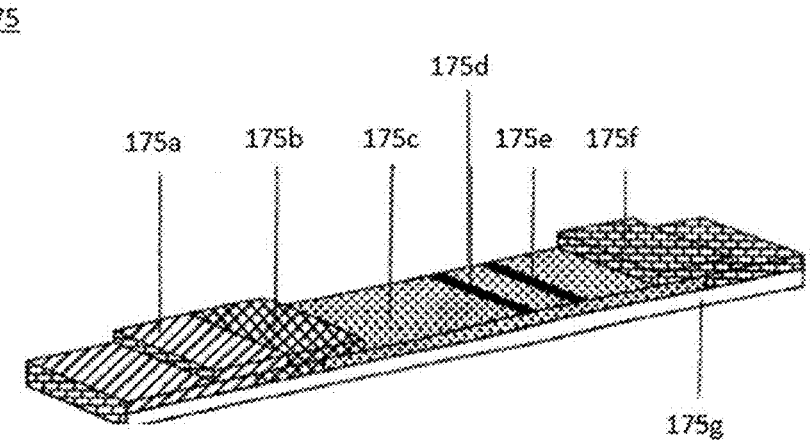
FIG. 3B is a schematic diagram illustrating elements of a conventional lateral flow device as may be used in accordance with the present disclosure.

FIG. 3B provides a schematic drawing illustrating a conventional LFD device 175 as described for example in International Patent Application No. PCT/IB2014/002637. The LFD 175 is formed on a substrate 175*g*, and includes a sample pad 175*a* for receiving and holding a sample fluid. Once sample pad 175*a* is saturated, the sample fluid migrates to conjugate pad 175*b*, which includes a bio-active conjugate for reacting with target molecules in the sample fluid and causing an analyte to bind with the molecules as they migrate via a chromatographic membrane 175*c* toward a test line 175*d*. An immobilizing or capture molecule at the test line 175*d* further binds with the molecule, causing the target molecules to accumulate at the test line 175*d* and express a color change for example resulting from the addition of the substrate of a linking enzyme. A control line 175*e* accumulates analyte that was not captured by the test line 175*d* to verify that the analyte was present and active, even in the case where no immobilized molecules appear at the test line 17*d*. An absorption pad 175*f* is provided at a terminus of the LFD to capture waste materials.

As illustrated in FIG. 3A, LFD 175 is contained within a single one of the sealed chambers 131-135 and may be used, for example, to separate certain components of the materials in that chamber. LFD 176 spans several of the sealed chambers, and may be used to distribute certain components among these chambers. For example, the sample and conjugate pads of LFD 176 may be provided in a first chamber, the membrane and test line provided in a second chamber, and the absorption pad in a third chamber. In another application illustrated in FIG. 3A, LFD 177 extends both within and outside of a single sealed chamber, and may be used to assist in the transfer of certain components of the materials either into or out of the chamber. For example, the sample pad of the LFD 177 may be inserted into the chamber to receive a sample fluid, while all other elements of the LFD 777 are positioned outside of the chamber.

Figure 4:
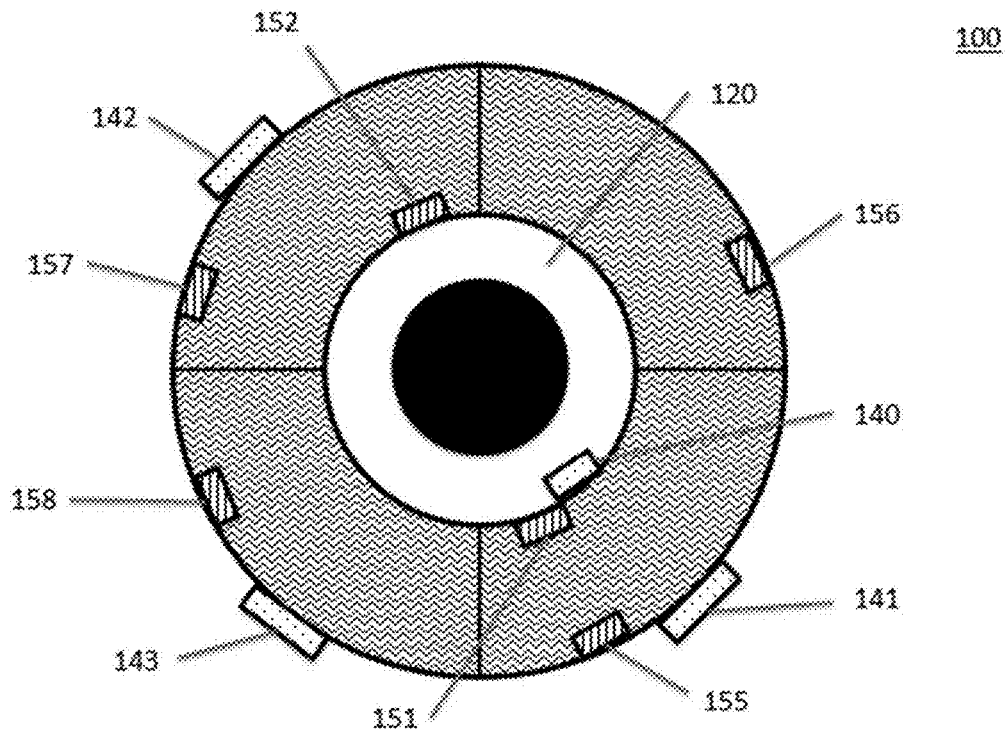
FIG. 4 is a schematic diagram illustrating further aspects of the present disclosure.

FIG. 4 illustrates additional elements of the mixing device 100 that provide for the movement and transfer of material between chambers. As depicted, outer compartments 141-143 are rotatably movable about the longitudinal axis of the mixing device 100. For example, outer compartments 141-143 may be individually coupled to rotational driving element. Alternatively, one or more of the outer compartments may be carried in a carrier 144 (not shown) formed as a toroidal ring that surrounds the ring 110 and is driven by the rotational driving element.

When placed in proximity to one of the chamber ports 155-158, one of the outer compartments 141-143 may be configured in an open state such that an inner volume of the compartment is placed in open communication with an inner volume the outer port, which has also been placed in an open state. Preferably, each of the outer ports 155-158 and outer compartments 141-143 may also be selectively placed in a closed state when not in proximity to one another.

According to one aspect of the present disclosure, one of the outer compartments 141-143 may be configured to be placed in a closed state by moving the outer compartment radially away from one of the chamber ports 155-158 such that it effectively seals against the outer edge of the ring 110. This approach may be optionally coupled with a complementary mechanical closure mechanism for outer ports 155-158 that returns the ports 155-158 to a closed state when the corresponding ones of the outer compartments 141-143 are moved away the ports (for example, closing one of the ports 155-158 by means of a spring-biased door that is initially opened by a mechanical arm engaged by one of the compartments 141-143 when in proximity to the one port 155-158).

Alternatively, and according to another aspect of the present disclosure, each of the outer compartments 141-143 and the outer ports 155-158 may be provided with a deformable element that assumes a normally closed, sealed state that can be changed to an open state by physically deforming the element so that the seal is disrupted. For example, in the present disclosure, corresponding elements in each of an outer compartment 141-143 and an outer ports 155-158 can be deformed by being brought into opposing, contacting proximity to one another. O-rings, for example as are commercially available from Apple Rubber of Lancaster, N.Y., are one suitable sealing element that can be used in this manner.

FIG. 4 in addition illustrates an inner compartment 140, which may optionally be provided to be rotatably movable about the longitudinal axis of the mixing device 100 along an interior edge of the ring 110. For example, the inner compartment 140 may be individually coupled to a rotational driving element. Alternatively, the inner compartments 140 may be carried in a carrier 145 (not shown) formed as a toroidal ring that is surrounded by the ring 110 and coupled to the rotational driving element.

As depicted, the inner compartment 140 is configured to be placed in an open state when in proximity to one of the interior ports 151, 152 and a closed state otherwise, for example employing the deformable elements described supra. The interior ports 151, 152 may be configured to place in an open state either in response to receiving the inner compartment 140 in overlapping proximity, or otherwise to provide access to the inner chamber 120.

One or more of the ring 110, outer compartments 141-143 and inner compartment 140 may be formed from a plastic, metallic or metal foil material suitable for disposal after a single use. In addition, one or more of the ring 110, outer compartments 141-143 and inner compartment 140 or portions thereof may be formed from a transparent plastic material to facilitate observability of color changes and other material indicia of the state of the associated biological, chemical or biochemical reactions.

Figure 5:
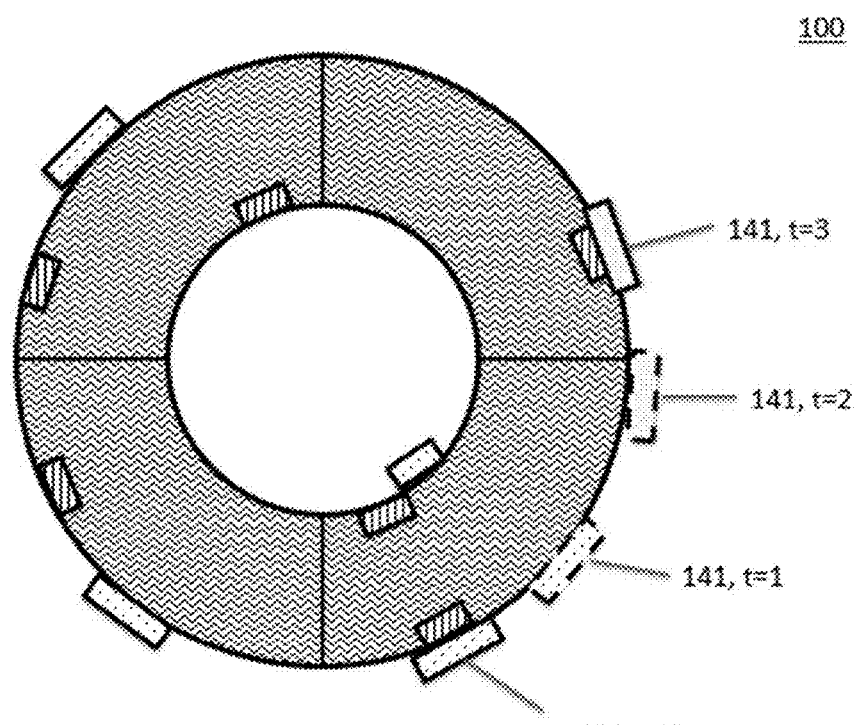
FIG. 5 is a schematic diagram illustrating further aspects of the present disclosure.

FIG. 5 illustrates a path for moving the outer compartment 141 between outer ports of adjacent chambers at successive times t=1, t=2, t=3 and t=4. On the path shown, material may be transferred from a first one of the two adjacent chambers to the outer compartment at time t=1, and then by the outer compartment to the second one of the adjacent chambers at time t=4.

Figure 6:
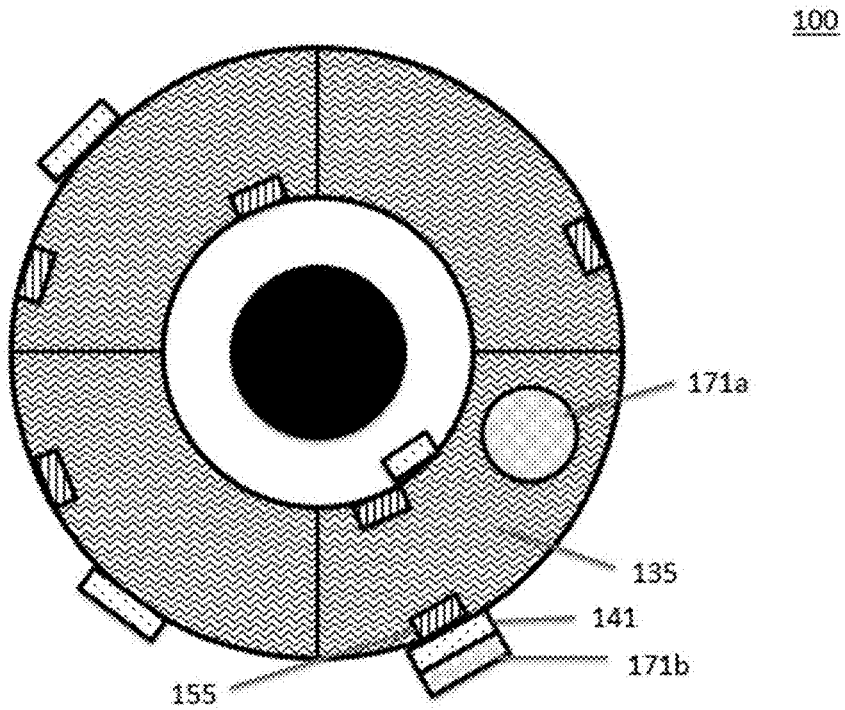
FIG. 6 is a schematic diagram illustrating further aspects of the present disclosure.

FIG. 6 illustrates some additional processing elements of the mixing device 100. Within sealed chamber 135, a first electromagnetic element 171a is provided. In addition, a second electromagnetic element 171b is provided as a component of outer compartment 155. In this configuration, magnetic materials (for example, a biological material adhered to solid phase reversible immobilization (SPRI) beads such as DYNABEADS magnetic beads available from Life Technologies of Frederick, Md.) may be drawn from the outer compartment 155 into the chamber 135 by activating the first electromagnetic element 171a to exert an attractive magnetic force, and either de-activating the second electromagnetic element 171b or activating the element 171b to exert a repellant magnetic force. Conversely, the magnetic material may be drawn from the chamber 135 into the outer compartment 155 by activating the second electromagnetic element 171b to exert an attractive magnetic force, and either de-activating the second electromagnetic element 171a or activating the element 171a to exert a repellant magnetic force. In this manner, for example, the material movement between adjacent chambers as described with reference to FIG. 4 can be accomplished.

While the electromagnetic element 171a of FIG. 6 is illustrated as a circular element, it should be noted that elements of alternate shapes and sizes are also contemplated by the present disclosure. Other processing elements may substitute for or supplement electromagnetic elements 171 as depicted in FIG. 6. For example, the electromagnetic elements may be replaced or supplemented by heating or cooling elements as previously described with reference to FIG. 1.

As an alternative to using electromagnetic elements (for example, in the case of moving non-magnetic materials), movement of the materials from the chamber 135 to the outer compartment 155 may be accomplished by synchronously spinning the ring 110 and outer compartment 155 (for example, by means of the rotational driving element 180 of FIG. 2) to generate a centripetal force that moves the material in the chamber 135 outwardly toward the outer compartment 155. Alternatively, a similar effect may be achieved by applying a driving element to shake, vibrate or provide a mechanical impulse the chamber 135, or by increasing an ambient pressure within the chamber 135 relative to the ambient pressure in the outer compartment 155.

In another aspect of the present disclosure, multiple chambers are vertically stacked along the center line to accommodate more complex material preparation procedures. Each chamber preferably includes one or more movable compartments in proximity to one or more of the outer and inner surfaces of each chamber. The movable compartments may be configured to move vertically between the layers of chambers. Alternatively, materials may be transferred between chambers by any of a variety of means including gravity, positive or negative differential pressures (for example, fluid-generated or across membranes), centripetal force or magnetic force. The vertically-arrayed chambers may have uniform diameters and form a cylindrical array, or have non-uniform diameters to form for example a conical array. An exemplary cylindrical array is described infra.

Figure 7:
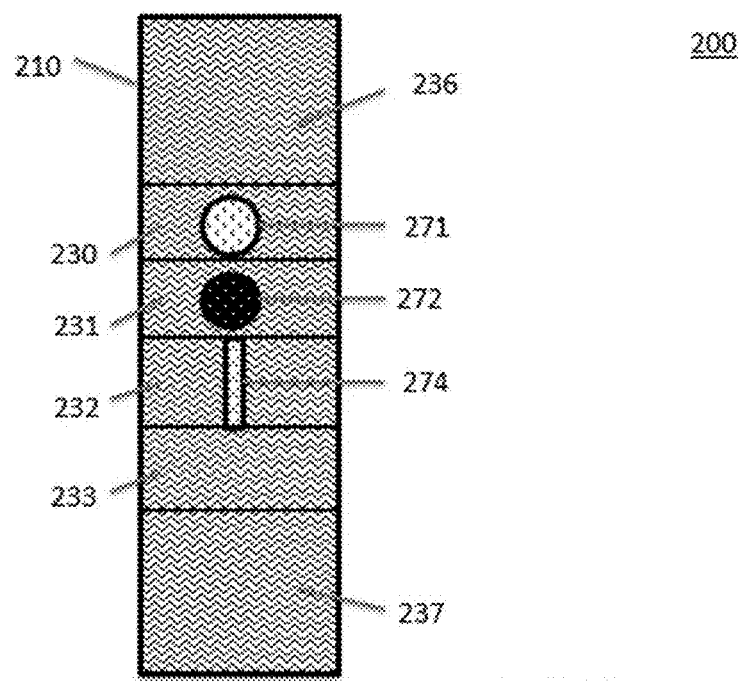
FIG. 7 is a schematic diagram illustrating a second configuration of a mixing device of the present disclosure.

FIG. 7 illustrates a second exemplary mixing device 200 in accordance with additional aspects of the present disclosure. The mixing device 200 includes a series of sealed chambers 230-233 that are linearly arrayed within a mixing member 210. One of skill in the art will readily understand that a variety of numbers and configurations of the sealed chambers 230-233 are contemplated by the present disclosure, and may be either uniformly sized or otherwise sized for example to store liquid or solid materials of a particular volume or mass. Optionally, the numbers and sizes of the sealed chambers 230-233 may be varied by employing adjustable inner walls that separate the chambers.

In the mixing member 210, the linearly-arrayed chambers 230-233 are positioned between wing members 236, 237. As described supra with reference to the first exemplary mixing device 100 of FIG. 1, elements selected from the group including electromagnetic elements 271, heating elements 272, cooling elements 273, membrane elements 274 or LFDs 275 (not shown) may be provided in ones of the sealed chambers 230-233 in accordance with the anticipated mixing process steps that will be carried out by the mixing device 200.

Figures 8A, 8B:
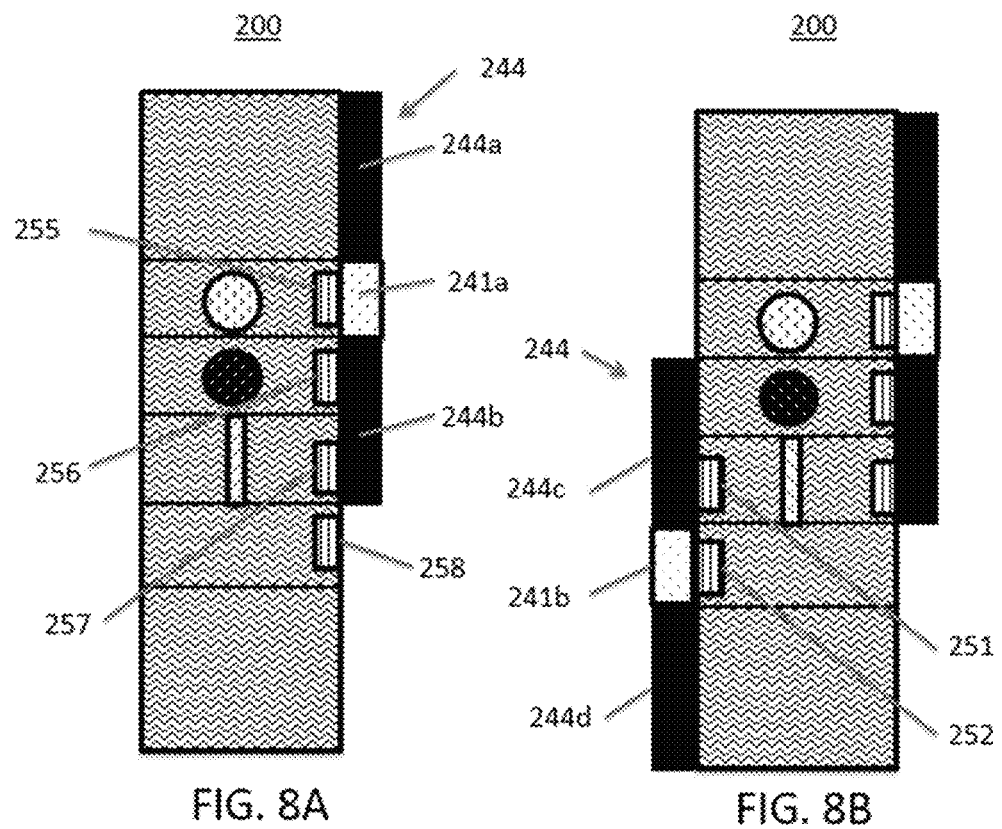
FIGS. 8A and 8B are schematic diagrams illustrating additional aspects of the present disclosure.

FIGS. 8A and 8B illustrate additional elements of the second exemplary mixing device that are contemplated by the present disclosure. The linearly-arrayed chambers 230-233 of the mixing member 210 are respectively provided with chamber ports 255-258 arranged along a linear side edge of the mixing member 210. A compartment 241a is provided in a carrier 244 having a linear side edge positioned in proximity to the linear side edge of the mixing member 210. The mixing device 200 is configured with one of the carrier 244 or the mixing member 210 being linearly translatable relative to the other. Linear translation may be provided for example by a driving system including a linear actuator coupled to a servo motor, as is available for example from Rockwell Automation, Inc., Milwaukee, Wis.

As shown in FIG. 8B, the mixing member 210 may include additional chamber ports 251, 252 arranged along another opposing linear side edge of the mixing member 210, against which another carrier 244 and compartment 241b is proximally positioned. At least one of the compartments 241a, 241b when in proximity to one of the ports 251, 252 or 255-258 may be selectively placed in an open state such that an inner volume of the compartment 241a or 241b is in open communication with an inner volume of the proximally-placed port 251, 252 or 255-258, which has also been placed in an open state. Preferably, each of the ports 251, 252 and 255-258 and compartments 241a, 241b may also be selectively placed in a closed state when not in proximity to one another.

As described supra, in order to provide open and closed states, one of more of the ports 251, 252 and 255-258 and compartments 241a, 241b may be fitted with a deformable element that normally assumes a closed, sealed state which can be changed to an open state by physically deforming the element so that the seal is disrupted. O-rings may be particularly suitable for this purpose. With reference to FIGS. 8A and 8B, for example, when ports 251, 256 and 257 are not in proximity to either or compartments 241a, 241b, wings 244a, 244b of the carriers 244 are in proximity to and effectively seal the closed ports 251, 256 and 257. Wing members 236, 237 of the mixing member 210 are provided to accommodate the wings 244a, 244b of the carriers 244 when the compartments 241a, 241b are positioned in proximity to the ports 252, 255 or 257 in outermost chambers 230, 233.

By way of example, FIG. 9 presents a flow diagram illustrating a conventional, manually-performed procedure 900 for preparing a blood material for immunoassay. At step 910, a lysis step is carried out for dissolving the blood material by combining 10 µl of blood material with a guanidine thiocyanate (GuSCN) solution having a concentration of 4.5 M. The mixture is pipetted five times, and allowed to sit for approximately 30 seconds before proceeding to step 920. At step 920, the mixture is combined with a mixture including 0.2 mg of DYNABEADS, 400 µl of 2-propanol and 200 µl of a binding buffer including salt (NaCl) in a concentration of 1.25 M and tris(hydroxymethyl)aminomethane (Tris) in a concentration of 30 mM and having a pH of 7.0. This mixture is allowed to sit at room temperature for approximately one minute, and results in binding the dissolved blood material to the DYNABEADS.

At step 930, the mixture is washed in a solution including one ml of a GuSCN wash buffer and one ml of ethanol (EtOH) by pipetting the mixture up and down three times. This mixture is then placed on a separator to separate the active materials from the wash and other waste materials. Finally, at step 940, the blood materials are extracted from DYNABEADS in an elution step that is carried out by placing the DYNABEADS in a solvent (100 µl of a water heated to 90° C.) for three minutes. The DYNABEADS can then be removed to obtain a blood material solution that can be subjected to the immunoassay. Carried out manually, the procedure 900 might easily extend over a time period of 30 minutes or more.

Figure 10A:
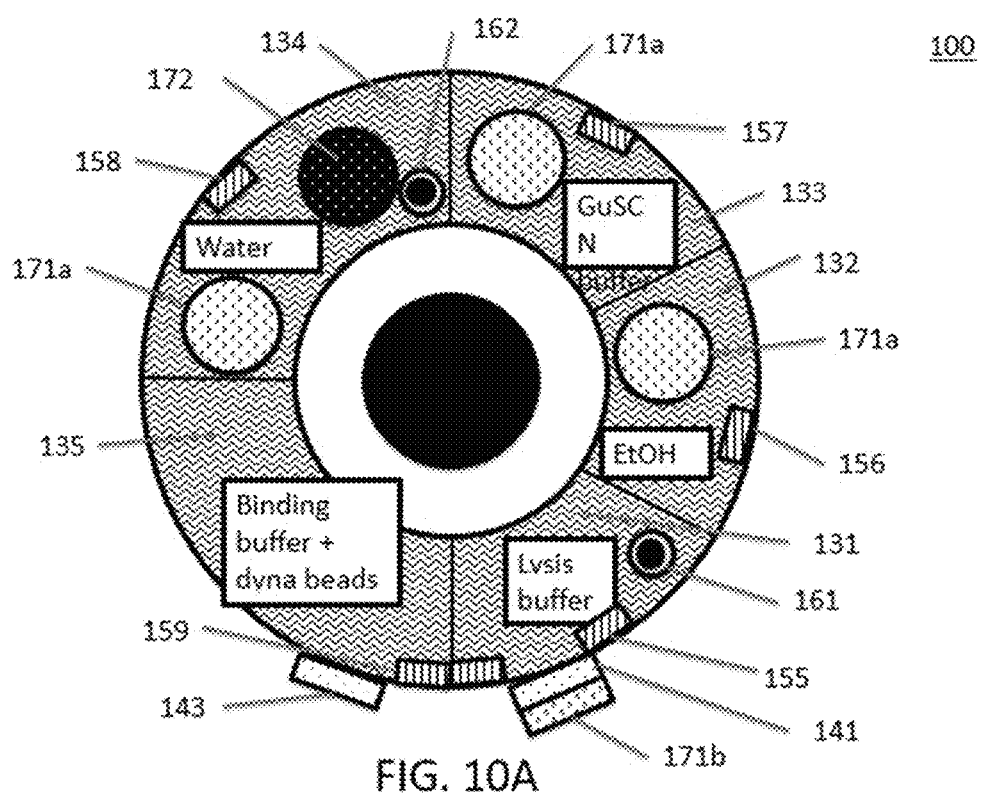
FIG. 10A is a schematic diagram illustrating a mixing device according to aspects of the present disclosure, configured for providing an automated process for preparing the blood product of FIG. 9.
Figure 10C:
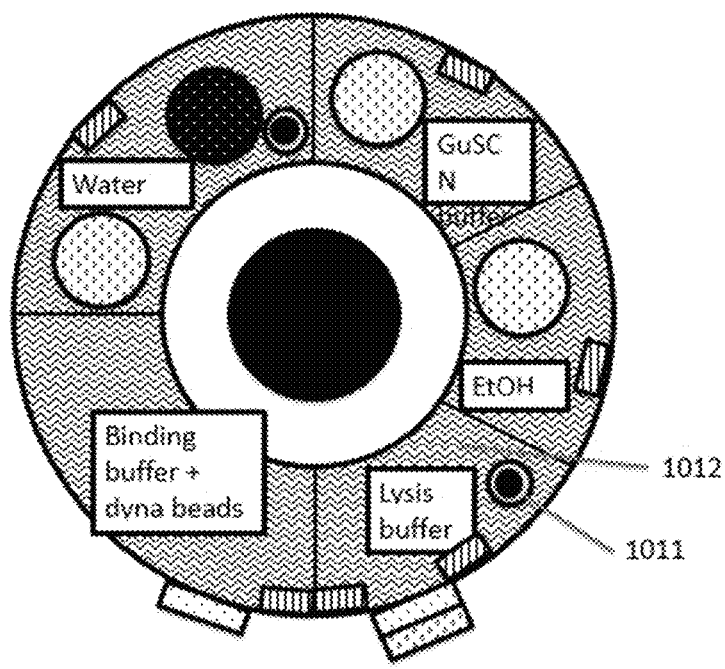
FIGS. 10C-10H are schematic diagrams illustrating additional states of the automated process of FIG. 10B.
Figure 10D:
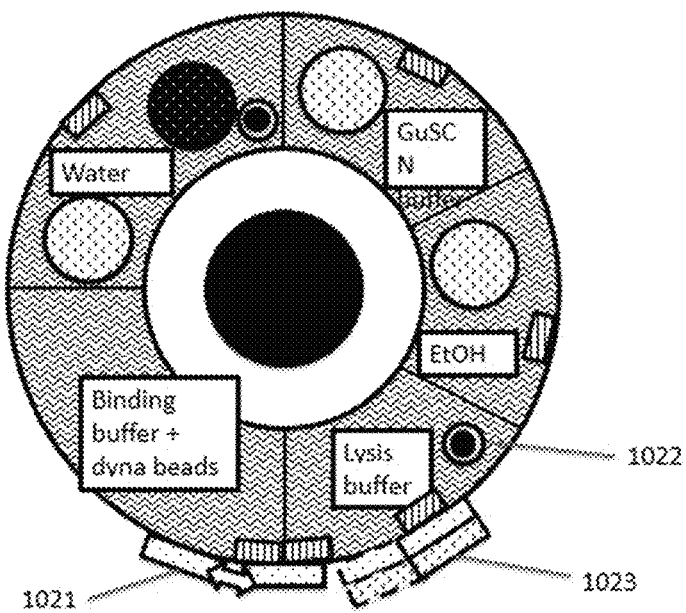

In accordance with the present disclosure, FIG. 10A discloses a mixing device 100 for preparing the blood material of FIG. 9. FIG. 10B presents a flow diagram illustrating an automated procedure for using the mixing device 100 of FIG. 10A to prepare the blood material. The procedural steps of FIG. 10B are further described with reference to the schematic diagrams of FIGS. 10C-10H.

As depicted in FIG. 10A, the mixing device 100 includes chambers 131-135, which are used to carry out the procedural steps depicted by the flow diagram of FIG. 10B. Chamber 131 is associated with step 1010 of FIG. 10B, includes an interactive port 161 and an outer port 155, and contains a certain quantity of lysis buffer material. Outer compartment 141 is positioned near to the outer port 155. The outer compartment 155 includes a magnetic element 171b. In step 1010 of FIG. 10B, and within chamber 131, a lysis process is carried for dissolving 10 µl of the blood material with a lysis buffer material (a GuSCN solution having a concentration of 4.5 M). As illustrated with reference to FIGS. 10A-C, these materials are introduced into the chamber 131 via interactive port 161 (step 1011). At step 1012, the materials are mixed (for example, five times by spinning the mixing member of device 100 in short cycles), and allowed to sit for approximately 30 seconds before proceeding to step 1020.

Chamber 135 is associated with step 1020 of FIG. 10B, includes an outer port 159 adjacent to an outer compartment 143. With reference to FIGS. 10A, B and D, the mixture in chamber 131 is transferred at step 1021 to compartment 143 (for example, by synchronously spinning both the mixing member and outer compartment 143). Compartment 143 is then moved from outer port 155 to outer port 159 so that the mixture can be transferred to chamber 135 (for example, by orienting the mixing device so that the outer compartment 143 is vertically above the chamber 135). Once transferred to chamber 135, the mixture is combined with a mixture including 0.2 mg of DYNABEADS, 400 µl of 2-propanol and 200 µl of a binding buffer including a NaCl in a concentration of 1.25 M and Tris in a concentration of 30 mM, and having a pH of 7.0. This mixture is allowed to sit at room temperature for approximately one minute before moving on to step 1030.

Figure 10E:
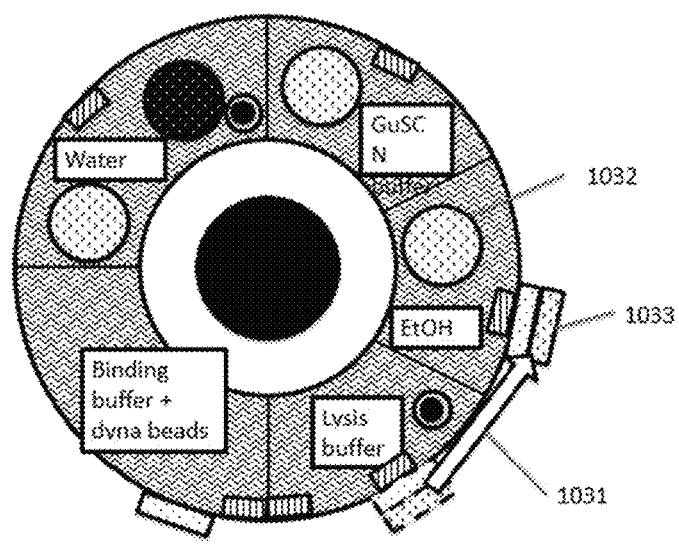
Figure 10F:
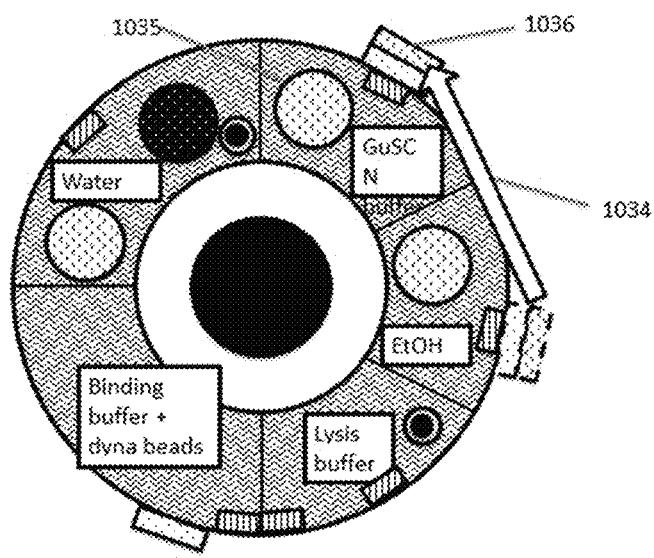

Chambers 132, 133 are associated with step 1030 of FIG. 10B. Chamber 132 includes an outer port 156 and magnetic element 171a, and contains a certain quantity of EtOH. Chamber 133 includes an outer port 157 and a magnetic element 171a, and contains a certain quantity of GuSCN. With reference to FIGS. 10A, B and D, the mixture in chamber 135 is transferred to compartment 141. With additional reference to FIG. 10E, compartment 141 is moved at step 1031 from outer port 159 to outer port 156 to transfer the mixture to chamber 132 by engaging the magnetic element 171a of chamber 132 at step 1032. In chamber 132, the material is washed in a solution containing 1 ml of EtOH. At step 1033, the washed material is transferred back via outer port 156 to the compartment 141 by engaging the magnetic element 171b of compartment 141. Because the active elements of the mixture have adhered to the DYNABEADS, the material can be transferred between the chambers 132, 133 and outer compartment 141 by moving the magnetically-influenced DYNABEADS via the magnetic elements 171a, b.

With reference to FIGS. 10A, B and F, the mixture in compartment 141 is next transferred at step 1034 to chamber 133 at step 1036 via port 157 for washing in a solution containing one ml of a GuSCN wash buffer. The transfer is accomplished by engaging the magnetic element 171a of chamber 133 step 1035. In each of the chambers 132, 133, the mixtures may be mixed for example by spinning the mixing member of device 100 in short cycles (for example, three cycles in each case). After washing is completed in chamber 133, the mixture is placed on a separator to separate the active materials from the wash and other waste materials, and is then returned to the compartment 141 at step 1036 (for example, by engaging the magnetic element 171b of compartment 141).

Figure 10G:
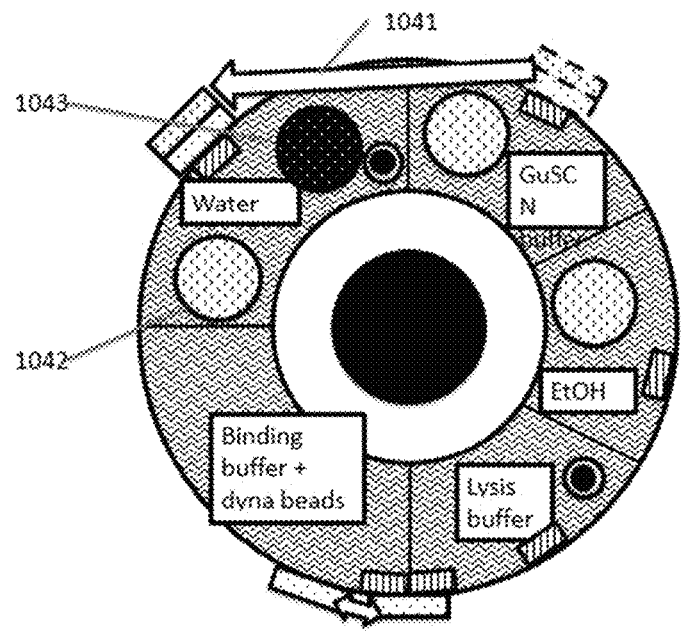
Figure 10H:
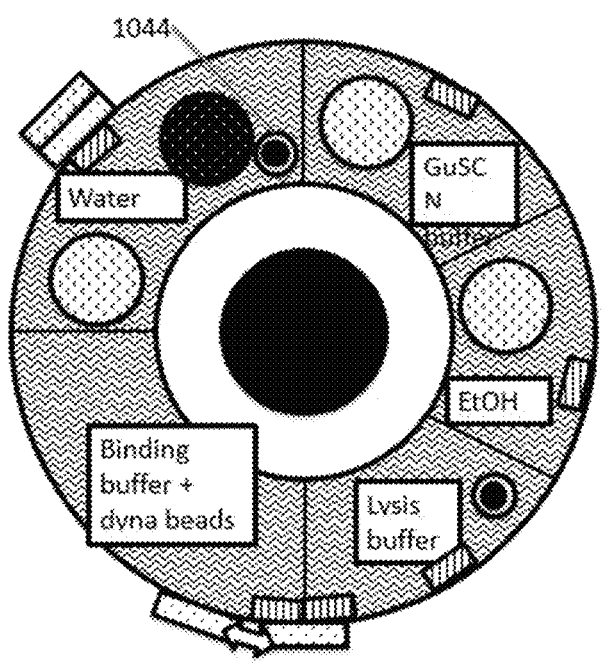

Chamber 134 is associated with step 1040 of FIG. 10B, and includes an outer port 158, a magnetic element 171a, a heating element 172 an interactive port 162, and a certain quantity of water. After the active materials are returned to the compartment 141 at step 1036, the compartment 141 is moved to the port 158 of chamber 134 at step 1041 as illustrated in FIG. 10G. The blood materials are drawn into the chamber 134 for example by engaging the magnetic element 171a at step 1042, and the elution step 1040 that is carried out by placing the DYNABEADS in a solvent (100 μl of a water heated to 90° C. by a heating element 172 for three minutes at step 1043. The DYNABEADS can then be removed (for example, via the compartment 141 and magnetic element 171b) to obtain a blood material solution that can be subjected to the immunoassay. While if carried out manually, the process 1000 of FIG. 10B might extend over a time period of 30 minutes or more, experience suggests that the process can be completed in as little as eight minutes when carried out using the claimed device.

In accordance with additional aspects of the present disclosure, and as initially described supra, multiple ring members may be vertically stacked to accommodate more complex material preparation procedures. For example, and as illustrated in FIGS. 11A and 11B, first and second mixing devices 100, 200 can be further arranged in multiple mixing-member stacked arrangements 100', 200'. While FIGS. 11A and 11B respectively illustrate stacked arrangements 100', 200' each having two stacked mixing members 110, 210, the stacked arrangements 100', 200' may alternatively include a greater number of mixing members 110, 210. In addition, the stacked arrangements 100', 200' may include stacked mixing members of different sizes. For example, the stacked arrangement 100' may include toroidal ring mixing members 110 of varying diameters (for example, in an order of increasing diameters such that the stacked arrangement assumes a conical profile).

An advantage of the stacked arrangements 100' 200' is that these arrangements effectively increase the number of chambers available to carry out process steps for complex mixing processes having many distinct steps. The contents of one of the chambers in an upper one of the mixing members 110, 210 may be transferred to a chamber in an adjacently lower one of the mixing members 110, 210 by various conventional arrangements. For example, a needle valve 191 may be provided to extend from a lower surface of a chamber in the upper mixing member, with a corresponding bladder 192 provided in an upper surface of the corresponding adjacently lower mixing member. The needle valve 191 may be inserted into the bladder 191 (for example, by moving the upper and adjacently lower mixing members toward each other by means of a driving unit including a linear actuator as described supra). Air or another pressurized gas may then be introduced into the chamber in the upper mixing member (for example, via another needle valve/bladder pairing) to move material from this chamber to the chamber in the adjacently lower mixing member.

Figure 12A:
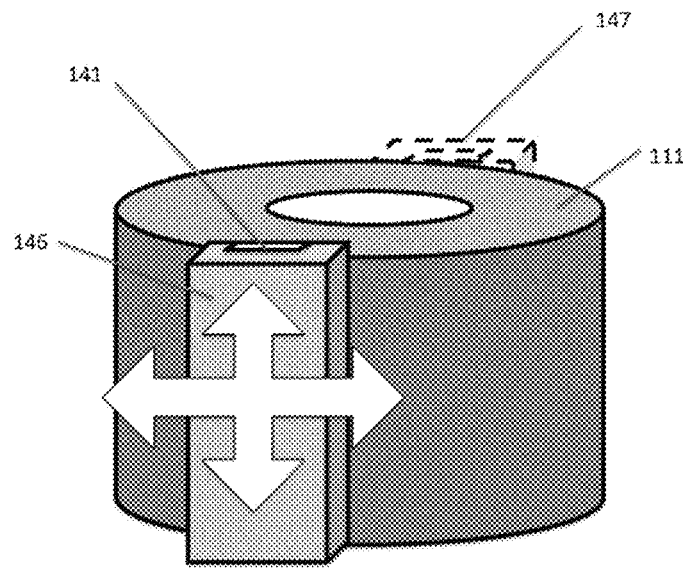
FIGS. 12A and 12B are schematic diagrams illustrating additional aspects of the present disclosure relating to the positioning of an outer compartment of a mixing device in accordance with aspects of the present disclosure.
Figure 12B:
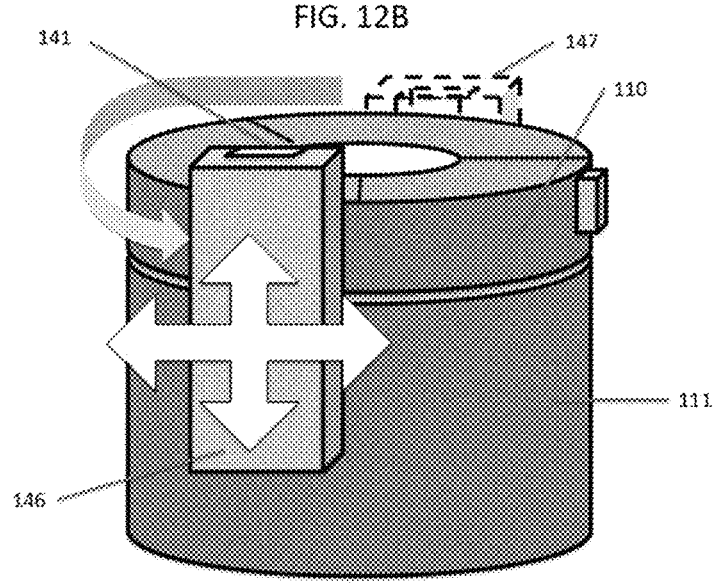

In accordance with the present disclosure, FIG. 12B illustrate a mixing device 100 that includes a single mixing member 110 and a driving ring 111 for manipulating a position of an outer compartment 141 along a periphery of the mixing member 110. The driving ring 111, which is also illustrated in FIG. 12A, is coupled to a compartment carrier 146, 147 that is rotatable with the driving ring 111 about a longitudinal axis of the device 100. Carrier 146, 147 is upwardly and downwardly movable in a direction parallel to the longitudinal axis to surround and engage or be disengaged from the outer compartment 141. It is envisioned that the outer compartment 141 may be fixed in a vertical position relative to the mixing member 110, but freely rotatable around the periphery of the mixing member 110 in order to be selectively aligned with one of the chamber ports described supra that is positioned around the periphery of the mixing member 110. For example, the compartment 141 and mixing member 110 may be coupled in a captive track arrangement that allows the compartment 141 to be rotatable around the periphery of the mixing member 110 without de-coupling from the member 110. As depicted in FIG. 12B, compartment carrier 146 is moved vertically upwardly to engage the compartment 141 and vertically downwardly to disengage from the compartment 141.

Figure 13A:
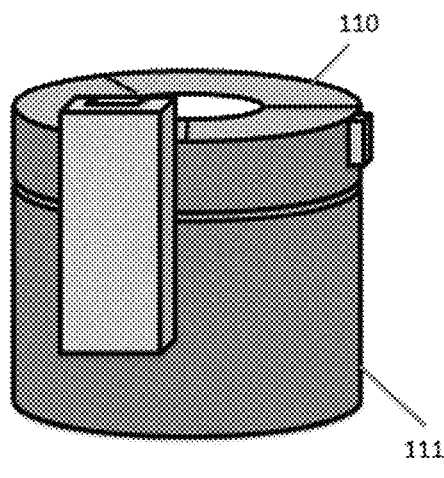
FIGS. 13A and 13B are schematic diagrams illustrating orientations of the mixing device illustrated by FIGS. 12A and 12B.
Figure 13B:
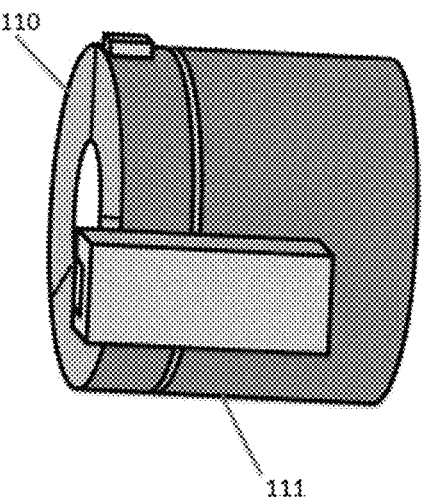

In accordance with the present disclosure, it may be advantageous to change an axial orientation of the mixing devices 100, 200 as illustrated in FIGS. 4, 8A and 8B. For example, the mixing member 110 of the mixing device 100 is normally positioned to be rotatable around the vertically-oriented longitudinal axis of the device 100. If the device 100 is rotated 90° such that the longitudinal axis assumes a horizontal orientation, a transfer of material from one of the chambers 131-135 to one of the outer compartments 141-143 can be accomplishing by rotating the one chamber and the one vertical compartment to their lowest vertical positions. In this position, the one chamber lies above the compartment, so that gravitational force will urge the material from the chamber to the compartment. FIGS. 13A and 13B respectively illustrate the mixing device 100 in the described initial and rotated positions To accommodate compartments 141-143 of potentially varying widths, the compartment carriers 146, 147 of FIGS. 12A, 12B may be provided with adjustable features for engaging the compartments 141-143. In accordance with the present disclosure, FIGS. 14A-14C illustrate one such adjustable engagement structure of the compartment carrier 146, 147, including an adjustable pin matrix as may be available, for example, from Matrix Gmbh Stuttgart, Ostfildern, Germany.

REFERENCE CHARACTER TABLE

The following Table 1 lists the reference characters and names of features and elements used herein:

TABLE 1

| Ref. char. | Feature or element |
|---|---|
| 100, 100' | first mixing devices |
| 110 | mixing member |
| 111 | driving ring |
| 120 | inner chamber |
| 131-135 | chambers |
| 140 | inner movable compartment |
| 141-143 | outer movable compartments |
| 144, 145 | compartment rings |
| 146, 147 | compartment carriers |
| 151-154 | inner ports |
| 155-159 | outer ports |
| 161, 162 | interactive ports |
| 171a, b | electromagnetic elements |
| 172 | heating element |
| 173 | cooling element |
| 174a, b | membrane elements |
| 175-177 | lateral flow devices |
| 175a | sample pad |
| 175b | conjugation pad |
| 175c | chromatographic (nitro cellulose) membrane |
| 175d | test line |
| 175e | control line |
| 175f | absorption pad |
| 175g | substrate |
| 180 | rotational driving element |
| 191 | needle valve |
| 192 | bladder |
| 193 | compartment carrier |
| 194 | pin matrix |
| 195 | first retracted pin set |
| 196 | first compartment cavity |
| 197 | second retracted pin set |
| 198 | second compartment cavity |
| 200, 200' | second mixing devices |
| 210 | mixing member |
| 230-233 | chambers |
| 236, 237 | wing members |
| 241a.b | compartments |
| 244 | carrier |
| 244a, b | carrier wings |
| 271 | electromagnetic element |
| 272 | heating element |
| 273 | cooling element |
| 274 | membrane element |
| 251, 252 | chamber ports |
| 255-258 | chamber ports |
| 900-940 | process and steps for conventional immunoassay blood material preparation procedure |
| 1000-1044 | process and steps for exemplary immunoassay blood material preparation procedure with mixing device |

It will be understood that, while various aspects of the present disclosure have been illustrated and described by way of example, the invention claimed herein is not limited thereto, but may be otherwise variously embodied within the scope of the following claims.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A device for manipulating one or more biological or chemical materials or a combination thereof, the device comprises:
    a mixing member having a plurality of chambers, each chamber having at least one chamber port along at least one side edge of the mixing member that may be selectively placed in an open state or a closed state; and
    at least one compartment movable externally along the at least one side edge of the mixing member for selective positioning in proximity to the ports along said side edge, the at least one compartment having a compartment port along a side of the compartment facing the one side edge of the mixing member, wherein:
    when the compartment port of the at least one compartment is moved to a position in overlapping proximity to the chamber port of a selected one of the chambers, the state of the chamber port of the selected chamber is changed from a closed state to an open state and the state of at least one of the chamber ports for another one of the plurality of chambers remains unchanged.

2. The device of claim 1, wherein:
    when the compartment port of the at least one compartment is moved to a position in overlapping proximity to the chamber port of the selected one of the chambers,
    an interior volume of the at least one compartment is placed in fluid communication with an interior volume of the selected chamber.

3. The device of claim 2, wherein at least one of the compartment port or the chamber port of the selected chamber comprises a deformable element.

4. The device of claim 3, wherein the deformable element comprises an o-ring.

5. The device of claim 2, wherein the state of the chamber port of the selected chamber is controlled by the application of one or more of heating, cooling, electrical power, mechanical force or magnetic influence.

6. The device of claim 2, wherein the plurality of sealed chambers of the mixing member are radially arrayed around a central axis to form a first toroidal ring.

7. The device of claim 6, wherein one or more of the at least one compartment or the first toroidal ring are rotatable about the central axis.

8. The device of claim 6, wherein the at least one compartment is provided in a second toroidal ring surrounding the first toroidal ring.

9. The device of claim 6, wherein the at least one compartment is provided in a second toroidal ring surrounded by the first toroidal ring.

10. The device of claim 6, comprising:
    at least two compartments, wherein
    a first one of the at least two compartments is movable about an outer circumference of the first toroidal ring; and
    a second one of the at least two compartments is movable about an inner circumference of the first toroidal ring.

11. The device of claim 10, wherein:
    the first one of the at least two compartments is provided in a second toroidal ring surrounding the first toroidal ring; and the second one of the at least two compartments is provided in a third toroidal ring that is surrounded by the first toroidal ring.

12. The device of claim 7, further comprising:
a driving unit for rotatably moving at least one of the first toroidal ring or the at least one compartment about the central axis.

13. The device of claim 12, further comprising:
a fixture for operably positioning the mixing member, the driving unit and the at least one compartment of the device relative to one another; and
a pivoting member coupled to the fixture for positioning and holding the fixture to selectively orient the central axis at least in either of vertical and horizontal positions.

14. The device of claim 13, wherein the pivoting member is further operable to position and hold the fixture for orienting the central axis between the horizontal and vertical positions.

15. The device of claim 13, further comprising a controller for controllably operating at least one of the driving unit or the pivoting member.

16. The device of claim 12, further comprising an inner chamber having an outer edge extending in proximity to an interior one of the side edges of the mixing member.

17. The device of claim 15, wherein the driving unit is further configured to rotate the inner chamber about the central axis.

18. The device of claim 16, wherein:
the inner chamber comprises a chamber port for selective positioning in proximity to the at least one chamber port provided along the interior side edge of the mixing member, wherein a state of the chamber port of the inner chamber selectively is selectively changeable to assume either of an open state or a closed state.

19. The device of claim 18, wherein the chamber port of the inner chamber and the at least one chamber port along the interior side edge of the mixing member comprise deformable elements.

20. The device of claim 19, wherein the deformable elements comprise o-rings.

21. The device of claim 18, wherein the state of at least one of the chamber port of the inner chamber or the at least one chamber port along the interior side edge of the ring is controlled by one or more of the application of heating, cooling or magnetic influence.

22. The device of claim 2, wherein:
the plurality of sealed chambers of the mixing member are linearly arrayed;
at least one of the one or more side edges of the mixing member is a linearly-extending, planar side edge; and
the at least one compartment is movable along the at least one linearly-extending, planar side edge.

23. The device of claim 22, wherein one or more of the at least one compartment or the mixing member is linearly translatable along or parallel to a longitudinal centerline of the device.

24. The device of claim 22, wherein the at least one compartment is provided in a carrier, the carrier comprising a linearly-extending, planar side wall extending in proximity to and along the at least one linearly-extending, planar side edge of the mixing member.

25. The device of claim 24, wherein:
when the at least one compartment is moved to a selected position in proximity to one of two or more chamber ports along the at least one side edge, the carrier sealably abuts the others of the two or more chamber ports.

26. The device of claim 22, wherein
the mixing member comprises two opposing, linearly-extending planar side edges;
two or more chamber ports are positioned along each of the two opposing, linearly-extending planar side edges of the mixing member; and
the device comprises two compartments respectively provided in two carriers each movable in proximity to one of the two opposing, linearly-extending planar side edges.

27. The device of claim 23, further comprising:
a driving unit for translatably moving one or more of the mixing member or the carrier.

28. The device of claim 27, further comprising:
a fixture for operably positioning the mixing member, the driving unit and the at least one compartment of the device relative to one another; and
a pivoting member coupled to the fixture for selectively and rotatably pivoting fixture about the longitudinal centerline of the device.

29. The device of claim 28, wherein the fixture is rotatably pivotable along the longitudinal axis by up to approximately 90 degrees.

30. The device of claim 28, further comprising a controller for controllably operating at least one of the driving unit or the pivoting member.

31. The device of claim 1, wherein or more of the mixing member or the at least one compartment comprise a material selected from the group consisting of metals, metal foils and plastics.

32. The device of claim 1, wherein at least one of the sealed chambers includes an element selected from the group consisting of heating elements, cooling elements, and magnetic elements.

33. The device of claim 1, wherein the at least one compartment includes an element selected from the group consisting of heating elements, cooling elements, and magnetic elements.

34. The device of claim 1, wherein at least one of the chambers includes a membrane.

35. The device of claim 1, wherein at least one of the chambers includes a lateral flow device (LFD).

36. The device of claim 1, wherein at least one of the chambers includes an absorption pad.

37. The device of claim 35, wherein the LFD extends across at least two of the chambers.

38. The device of claim 35, wherein the LFD extends externally from the at least one chamber.

39. The device of claim 1, further comprising a driving unit configurable to shake, vibrate or provide a mechanical impulse to one or more of the mixing member or the at least one compartment.

40. A device for manipulating one or more biological or chemical materials or a combination thereof, the device comprising:
two or more mixing members vertically aligned along a central axis, each mixing member including a plurality of chambers, each chamber having at least one chamber port along one of one or more side edges of the mixing member that may be selectively placed in an open state or a closed state; and
at least one compartment movable externally along one of the side edges of one of the mixing members for selective positioning in proximity to the chamber ports along the one side edge, the at least one compartment having a compartment port along a side of the one compartment facing the one side edge of the one mixing member.

41. The device of claim 40, wherein:
when the compartment port of the at least one compartment is moved to a position in overlapping proximity to the chamber port of a selected one of the chambers,
an interior volume of the at least one compartment is placed in fluid communication with an interior volume of the selected chamber.

42. The device of claim 40, wherein:
when the compartment port of the at least one compartment is moved to a position in overlapping proximity to the chamber port of a selected one of the chambers, the state of the chamber port of the selected chamber is changed from a closed state to an open state and the state of at least one of the chamber ports for another one of the plurality of chambers of the one mixing member remains unchanged.

43. The device of claim 41, wherein at least one of the compartment port or the chamber port of the selected one chamber comprises a deformable element.

44. The device of claim 43, wherein the deformable element comprises an o-ring.

45. The device of claim 41, wherein the state of the selected one chamber is controlled by the application of heating, cooling, electrical power, mechanical force or magnetic influence.

46. The device of claim 40, further comprising:
inter-mixer ports located on opposing surfaces of two adjacent ones of the two or more mixing members, wherein:
one or more of the adjacent mixing members is movable relative to the other mixing member, such that inter-mixer ports on opposing surfaces can be positioned in overlapping proximity to one another,
each inter-mixer port is in communication with one of the chambers in its respective mixing member, and
the overlapping inter-mixer ports in an open configuration enable the interior volumes of respective communicating chambers to be in fluid communication with one another.

47. The device of claim 46, wherein:
one of the inter-mixer ports located on one of the opposing surfaces of the two adjacent mixing members comprises a valve member; and
another one of the inter-mixer ports located on one of the opposing surfaces of the two adjacent mixing members comprises a bladder member,
wherein:
the adjacent mixing members are is movable relative to one another, such that the valve member can be aligned with and inserted through the bladder member; and
when the valve member is aligned and inserted through the bladder member, an interior volume of one of the two adjacent mixing members is in fluid communication with the other one of the two adjacent mixing members.

48. The device of claim 41, wherein the plurality of sealed chambers of each of the two or more mixing members are radially arrayed around the central axis to form first toroidal rings.

49. The device of claim 48, wherein one or more of the at least one compartment or at least one of the first toroidal rings is rotatable about a central axis of the first toroidal rings.

50. The device of claim 48, wherein:
the at least one compartment is provided in a second toroidal ring, and
the second toroidal ring surrounds one of the first toroidal rings.

51. The device of claim 48, wherein:
the at least one compartment is provided in a second toroidal ring, and
one of the first toroidal ring surrounds the second toroidal ring.

52. The device of claim 47, comprising:
at least two compartments, wherein
a first one of the at least two compartments is movable about an outer circumference of one of the first toroidal rings; and
a second one of the at least two compartments is movable about an inner circumference of the one first toroidal ring.

53. The device of claim 52, wherein:
the first one of the at least two compartments is provided in a second toroidal ring surrounding one of the first toroidal rings; and
the second one of the at least two compartments is provided in a third toroidal ring that is surrounded by the one first toroidal ring.

54. The device of claim 47, further comprising:
a driving unit for rotatably moving at least one of the mixing members or the at least one compartment about the central axis.

55. The device of claim 54, further comprising:
a fixture for positioning the mixing members, the driving unit and the at least one compartment of the device relative to one another; and
a pivoting member coupled to the fixture for selectively positioning and holding the fixture to orient the central axis at least in vertical and horizontal positions.

56. The device of claim 55, wherein the pivoting member is further operable to position and hold the fixture to orient the central axis between the horizontal and vertical positions.

57. The device of claim 55, further comprising a controller for controllably operating at least one of the driving unit or the pivoting member.

58. The device of claim 40, wherein:
the plurality of chambers of each of the mixing members are linearly arrayed;
at least one of the one or more side edges of one of the mixing members is a linearly-extending, planar side edge; and
the at least one compartment is movable along the at least one linearly-extending, planar side edge of the one mixing member.

59. The device of claim 58, wherein one or more of the at least one compartment or at least one of the mixing members is linearly translatable along or parallel to a longitudinal centerline of the device.

60. The device of claim 58, wherein the at least one compartment is provided in a carrier, the carrier comprising a linearly-extending, planar side wall extending in proximity to and along the at least one linearly-extending, planar side edge of the one mixing member.

61. The device of claim 60, wherein:
when the at least one compartment is moved to a selected position in proximity to one of two or more chamber ports along the at least one side edge, the carrier sealably abuts the others of the two or more chamber ports along the at least one side edge.

62. The device of claim 58, wherein
the one mixing member comprises two opposing, linearly-extending planar side edges;
two or more chamber ports are positioned along each of the two opposing, linearly-extending planar side edges of the one mixing member; and
the device comprises two compartments respectively provided in two carriers each movable in proximity to one of the two opposing, linearly-extending planar side edges.

63. The device of claim 60, further comprising:
a driving unit for translatably moving one or more of the one mixing member or the carrier.

64. The device of claim 63, further comprising:
a fixture for operably positioning the one mixing member, the driving unit and the at carrier relative to one another; and
a pivoting member coupled to the fixture for selectively and rotatably pivoting the fixture about the longitudinal centerline of the device.

65. The device of claim 64, wherein the mixing member is rotatably pivotable about the longitudinal axis by up to approximately 90 degrees.

66. The device of claim 64, further comprising a controller for controllably operating at least one of the driving unit or the pivoting member.

67. A method for manipulating a biological or chemical material or a combination material thereof, comprising:
placing the material in an interior volume of one of a plurality of chambers provided in a mixing member, each chamber having at least one chamber port along a side edge of the mixing member that may be selectively placed in an open state or a closed state;
transferring the material in the interior volume of the one chamber to an interior volume of an outer compartment positioned in proximity to the chamber port of the one chamber;
moving the outer compartment in proximity to the port of a second one of the plurality of chambers; and
transferring the first material in the interior volume of the outer compartment to an interior volume of the second chamber,
wherein during the transfer of the first material from the one chamber to the outer compartment and then to the second chamber, the state of at least another one of the chamber ports for another one of the plurality of chambers remains unchanged.

68. The method of claim 67, wherein:
the plurality of chambers of the mixing member are radially arrayed to form a toroidal ring; and
the first transferring step comprises rotating each of the ring and the outer compartment in synchrony at a common rotational speed, thereby causing the first material to move from the interior volume of the one chamber to the interior volume of the outer compartment by means of a centripetal force generated by rotating each of the ring and the outer compartment in synchrony.

69. The method of claim 67, wherein:
the material comprises a material adhered to solid phase reversible immobilization (SPRI) beads,
the outer compartment includes a magnetic element, and
the first transferring step comprises activating the magnetic element of the outer compartment, causing the material to move from the interior volume of the one chamber to the interior volume of the outer compartment under a magnetic force generated by the magnetic element.

70. The method of claim 67, wherein:
the first material comprises a material adhered to solid phase reversible immobilization (SPRI) beads,
the second chamber includes a magnetic element, and
the second transferring step comprises activating the magnetic element of the second chamber, causing the material to move from the interior volume of the outer compartment to the interior volume of the second chamber under a magnetic force generated by the magnetic element.

71. The method of claim 66, wherein the second chamber includes a heating element, further comprising:
activating the heating element for a predetermined time period after transferring the material to the interior volume of the second chamber.

72. The method of claim 67, wherein the second chamber includes a cooling element, further comprising:
activating the cooling element for a predetermined time period after transferring the material to the interior volume of the second chamber.

73. The method of claim 67, wherein the second chamber includes a membrane.

74. The method of claim 67, wherein the second chamber includes a lateral flow device (LFD).

75. The method of claim 74, wherein the LFD extends between adjacent ones of the plurality of chambers.

76. The method of claim 67, further comprising:
activating a driving unit to selectively shake, vibrate or provide a mechanical impulse to one or more of the mixing member or the at least one compartment.

77. The method of claim 67, further comprising:
transferring the material in the interior volume of the second chamber to an interior volume of one of a plurality of chambers provided in a second mixing member, wherein:
the one chamber of the second mixing member is vertically stacked below and in overlapping proximity to the second chamber of the mixing member, and
one or more of the mixing member and second mixing member is movable relative to the other mixing member, such that inter-mixer ports on opposing surfaces of the mixing member and second mixing member can be positioned in overlapping proximity to one another,
each inter-mixer port is provided in one of the second chamber in the mixing member or the one chamber in the second mixing member, and
the overlapping inter-mixer ports in an open state place the interior volumes of respective communicating chambers to be in fluid communication with one another, thereby enabling the transferring step.

78. The method of claim 77, wherein:
the inter-mixer port provided in the second chamber in the mixing member comprises a valve member; and
the inter-mixer port provided in the one chamber of the second mixing member comprises a bladder member.

* * * * *